US008129363B2

(12) United States Patent
Gao et al.

(10) Patent No.: US 8,129,363 B2
(45) Date of Patent: Mar. 6, 2012

(54) METHOD FOR OBTAINING CONJUGATED ESTROGEN MIXTURES FROM PREGNANT MARE URINE AND USE OF A MACROPOROUS RESIN IN THE METHOD

(75) Inventors: Xiaoli Gao, Xinjiang (CN); Jianmin Xiao, Xinjiang (CN)

(73) Assignee: Xinjiang Tefeng Pharmaceutical Co., Ltd., Urumqi, Xinjiang (CN)

( * ) Notice: Subject to any disclaimer, the term of this patent is extended or adjusted under 35 U.S.C. 154(b) by 1086 days.

(21) Appl. No.: 11/995,917

(22) PCT Filed: Dec. 5, 2006

(86) PCT No.: PCT/CN2006/003282

§ 371 (c)(1), (2), (4) Date: Jan. 16, 2008

(87) PCT Pub. No.: WO2007/065349

PCT Pub. Date: Jun. 14, 2007

(65) Prior Publication Data

US 2009/0131698 A1 May 21, 2009

(30) Foreign Application Priority Data

Dec. 6, 2005 (CN) .......................... 2005 1 0129373

(51) Int. Cl.
*A61K 31/56* (2006.01)

(52) U.S. Cl. ....................................................... 514/170

(58) Field of Classification Search ................... 514/170
See application file for complete search history.

(56) References Cited

U.S. PATENT DOCUMENTS

| | | | |
|---|---|---|---|
| 2,429,398 | A | 10/1947 | Outremont et al. |
| 2,519,516 | A | 8/1950 | Turner et al. |
| 2,696,265 | A | 12/1954 | Beall et al. |
| 2,711,988 | A | 6/1955 | Deans et al. |
| 2,834,712 | A | 5/1958 | Beall et al. |
| 5,723,454 | A | 3/1998 | Ban et al. |

FOREIGN PATENT DOCUMENTS

| | | | |
|---|---|---|---|
| CN | 1308083 | A | 8/2001 |
| CN | 1381240 | A | 11/2002 |
| CN | 1526721 | A | 9/2004 |

*Primary Examiner* — Barbara P Badio

(74) *Attorney, Agent, or Firm* — Knobbe Martens Olson & Bear LLP

(57) ABSTRACT

The present invention relates to a method for obtaining a natural mixture of conjugated estrogens from urine of pregnant mares (PMU) and use of a macroporous adsorption resin in the method. The method for obtaining a natural mixture of conjugated estrogen from PMU includes the steps of pretreating raw PMU; adsorbing the natural mixture of conjugated estrogens contained in PMU with a macroporous adsorption resin; washing the macroporous adsorption resin laden with the mixture of conjugated estrogens with an alkaline aqueous solution; and eluting the washed adsorption resin with an eluting agent to obtain the mixture of conjugated estrogens. The macroporous adsorption resin is a styrene-divinylbenzene semipolar macroporous adsorption resin with ester group structure. The method according to the invention solves the problems of low adsorptive capacity and high cost existed in the conventional methods, and is suitable for large-scale production.

7 Claims, No Drawings

METHOD FOR OBTAINING CONJUGATED ESTROGEN MIXTURES FROM PREGNANT MARE URINE AND USE OF A MACROPOROUS RESIN IN THE METHOD

RELATED APPLICATIONS

This application is a U.S. National Phase of International Application No. PCT/CN2006/003282, filed 5 Dec. 2006, designating the U.S. and published not in English 14 Jun. 2007 as WO 2007/065349, which claims the benefit of Chinese application No. 200510129373.X, filed 6 Dec. 2005.

TECHNICAL FIELD

The present invention relates to the field of biochemical pharmaceutics. Specifically, the present invention relates to a method for obtaining a natural mixture of conjugated estrogens from the pregnant mares' urine and use of a macroporous adsorption resin in the method.

BACKGROUND OF THE INVENTION

Studies on methods of extracting natural mixture of conjugated estrogens from pregnant mares' urine (PMU) have been reported since 1930s. Because of its definite therapeutic effect and safety reliability, mixture of natural conjugated estrogens is used in clinic for treating and preventing female physiological or artificial climacteric period syndrome occurred after menopause. The mixture can also be used to treat and prevent osteoporosis, the effect of which has been widely recognized. The extracting methods have been improved continuously during the past 70 years, especially for the recent years.

The early reports on methods of extracting conjugated estrogens mixture include U.S. Pat. No. 2,429,398, U.S. Pat. No. 2,519,516, U.S. Pat. No. 2,696,265, U.S. Pat. No. 2,711,988, U.S. Pat. No. 2,834,712, etc., where organic solvents were mainly applied for the purpose of extraction. After 1950s, active carbon, ion exchange resin, and reverse phase silica gel, etc. was used in methods for extracting a conjugated estrogens mixture from PMU. However, the adsorptive capacities achieved by these methods were low, which is not suitable for large-scale production.

In late 1990s, the application of new macroporous adsorption resin in obtaining mixture of conjugated estrogens from PMU showed great advantages. U.S. Pat. No. 5,723,454 (Ivan Ban., et al.) describes a method of obtaining a extract containing mixture of natural conjugated estrogens from PMU by using non-ion semipolar macroporous cross-linked polyacrylate resin; CN 1381240A (Song Walapa, et al.) describes a method of extracting conjugated estrogens mixture from PMU by polystyrene resin; CN1526721A (Zhou tao, et al.) describes an extracting method of obtaining mixture of conjugated estrogens, wherein polar adsorption resin containing sulfoxide group was used to extract the conjugated estrogens mixture from PMU, followed by eluting.

Generally, conventional method for extracting conjugated estrogens mixture with macroporous adsorption resin comprises the following steps: first, pretreating raw PMU; second, adsorbing conjugated estrogens mixture from PMU with a macroporous adsorption resin; third, washing the macroporous adsorption resin laden with the mixture of conjugated estrogens by an alkaline/neutral aqueous solution; and eluting the washed macroporous adsorption resin to obtain the conjugated estrogens mixture. Although these methods can obtain quickly and conveniently the enrichment component of natural conjugated estrogens mixture from PMU, it still could not solve the problems described below.

The contents of the conjugated estrogens mixture in PMU are quite different in diverse pregnancy periods. Urines of a pregnant mare in its 3-9 months' pregnancies (effective utilization period of PMU) were collected respectively and the contents of conjugated estrogens mixtures were tested. The contents of conjugated estrogens mixture of PMU in diverse pregnancy periods ranged from 30-300 mg/L. Within the best collecting period (5-7 months' pregnancies), the contents of conjugated estrogens mixture of PMU are generally above 100 mg/L, and even more.

Nevertheless, when conventional methods were used to treat PMU with relatively high contents of conjugated estrogens mixture, the adsorptive ratio of resin to PMU is rather low. Especially when the contents of the conjugated estrogens mixture is above 100 mg/L in PMU, the adsorptive ratio of resin to PMU will generally be less than 1:30. For large-scale production, this adsorptive ratio is difficult to satisfy practical requirement.

In addition, when conventional macroporous resins were used to adsorb PMU, impurities in PMU will also be adsorbed. Sometimes, the impurities even have preference to be adsorbed over the conjugated estrogens mixture due to the non-specific adsorption of the macroporous resin. Therefore, in order to improve adsorptive ratio, the raw materials used in conventional methods need to be pretreated, for instance, by adjusting PMU to a pH of above 10 with alkaline substances or by depleting cresol from PMU. All these procedures make the methods more difficult to operate, and fail to significantly improve the production efficiency.

Moreover, the resins used in conventional methods are relatively expensive, making no much difference in cost when compared to conventional solvent extracting processes.

Therefore, it is advantageous to improve the adsorptive ability of resin to conjugated estrogens mixture in PMU and to lower the cost. The present invention intends to solve the above-mentioned problems and therefore provide a method suitable for the large-scale manufacture of raw materials for pharmaceuticals production.

DISCLOSURE OF THE INVENTION

The present invention provides a method for obtaining the natural mixture of conjugated estrogens from PMU and use of a macroporous adsorption resin therein. In the method according to the invention, a pharmaceutically acceptable styrene-divinylbenzene semipolar macroporous adsorption resin with ester group structure is used to overcome the deficiencies in conventional methods. This method is very simple, without the need for complicated PMU pretreatment. Furthermore, the resin used in the method has strong adsorptive capability to conjugated estrogens mixture with various contents, and is very suitable for large-scale production.

The styrene-divinylbenzene semipolar macroporous adsorption resin with ester group structure is very stable and safe. The resin can work normally even under strong acidic/basic conditions and at high temperatures, without being degraded. Accordingly, even trace amount of toxic degradation product will be hardly released into the extract, which is used as raw material for drug production. The resin of the present invention meets the safety requirement for medicine use. After administration to rats for 6 month, no obvious toxic side effect was observed in routine blood test, biochemical blood test, and organs. The non-toxic dosage of the resin is 4 g/kg/d, very suitable for being used in drug manufacture.

The price of the styrene-divinylbenzene semipolar macroporous adsorption resin with ester group structure is very inexpensive, being only ¼-⅙ of the resins used in conventional arts. For instance, the average price of Amberlite XAD resin series and Dowex resin series is above 300 yuan/kg. The resin according to the present invention, in contrast, is less than 60 yuan/kg. Apparently, the resin of the present invention is more cost-effective.

In one aspect of the invention, there is provided a method of obtaining a conjugated estrogens mixture from PMU, comprising the steps of a. pretreating raw pregnant mares' urine; b. adsorbing a conjugated estrogens mixture from the pregnant mares' urine with a macroporous adsorption resin; c. washing the macroporous adsorption resin adsorbed with the conjugated estrogens mixture by an alkaline aqueous solution; and (d). eluting the macroporous adsorption resin to obtain the conjugated estrogens mixture, wherein the macroporous adsorption resin is selected from styrene-divinylbenzene semipolar macroporous adsorption resins with ester group structure.

In another aspect, the present invention provides the use of styrene-divinylbenzene semipolar macroporous adsorption resin with ester group structure in obtaining conjugated estrogens mixture from PMU.

In a preferred embodiment, the styrene-divinylbenzene semipolar macroporous adsorption resin with ester group structure can be obtained by polymerizing carboxylate and styrene-divinylbenzene.

In another preferred embodiment, the average diameter of the styrene-divinylbenzene semipolar macroporous adsorption resins with ester group structure is in the range of 50-120 Å, and the specific surface of the resin is in the range of 400-1000 $m^2/g$.

In still another preferred embodiment, the styrene-divinylbenzene semipolar macroporous adsorption resins with ester group structure is at least one selected from semipolar macroporous adsorption resin types of HPD-400, HPD-400A, HPD-450, HPD-100, and AB-8.

In step c, at temperature of 20° C. to 60° C., an alkaline aqueous solution with a pH of 11.0-14.0 is used to wash the macroporous adsorption resin adsorbed with conjugated estrogens mixture.

In step d, at temperature of 20° C. to 60° C., an aqueous solution of polar organic solvent of lower alcohols and/or lower ketones, which is miscible with water, is used to elute the macroporous adsorption resin to obtain the conjugated estrogens mixture. The pH of the solution used for elution is from 9 to 14. Inorganic bases, such as sodium hydroxide, potassium hydroxide, sodium carbonate, potassium carbonate, potassium bicarbonate, or sodium bicarbonate is used to adjust the pH. The volume ratio of the polar organic solvent to water is in the range of 90:10 to 20:80.

The alkaline aqueous solution mentioned above is an inorganic basic aqueous solution such as, sodium hydroxide aqueous solution, potassium hydroxide aqueous solution, sodium carbonate aqueous solution, potassium carbonate aqueous solution, potassium bicarbonate aqueous solution, or sodium bicarbonate aqueous solution. The washing volume of the alkaline aqueous solution is about 2 to 10 times that of the adsorption resin. The speed of the alkaline aqueous solution flowing through the container filled with the adsorption resin is 3-10 times volume of adsorption resin in 1 hour.

The lower alcohol used in the eluent is methanol, ethanol, n-propanol, iso-propanol, or butanol. The lower kenone used in the eluent is acetone or butanone. The amount of the eluent is 2-10 times volume of adsorption resin. The speed of the alkaline aqueous solution flowing through the container filled with the adsorption resin is 3-10 times volume of adsorption resin in 1 hour.

HPD-400, HPD-400A, HPD-450, and HPD-100 semipolar macroporous adsorption resins mentioned above are commercially available products of CangZhou Baoen company. AB-8 semipolar macroporous adsorption resin mentioned above is a commercially available product of the Chemical Plant of Tianjin University. The resins have the similar structural unit of formula I:

[I]

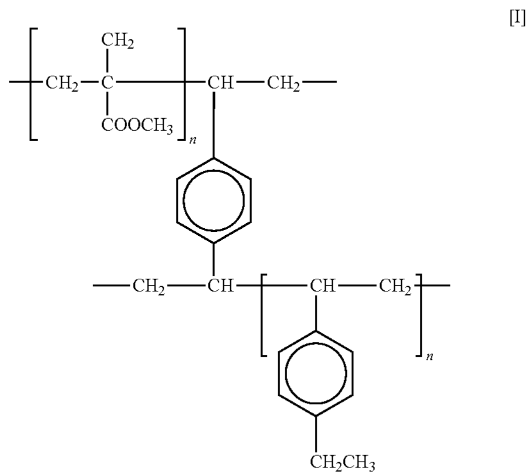

In the procedures of the present invention, the semipolar macroporous adsorption resin can be placed into a container so that the resin can be fully in contact with PMU. The PMU and the resin can be added in proportion, and mixed for a sufficient amount of time, which is called static state adsorption. Alternatively, the PMU can flow through the container filled with the adsorption resin in a constant speed, which is called dynamic adsorption. In the present invention, dynamic adsorption is preferred.

In the dynamic adsorption of the present invention, the flow speed of the PMU in the container filled with semipolar macroporous adsorption resin can be 1 to 10 parts PMU/1 part resin/1 hour. Preferably, the flow speed is 4 to 6 parts PMU/1 part resin/1 hour.

The semipolar macroporous adsorption resin of the present invention has superior ability of adsorbing conjugated estrogens mixture from PMU. In dynamic adsorption, one part of the resin can adsorb up to 150 parts by volume of PMU. Preferably, the adsorption is carried out at a ratio of 40-100 parts PMU/1 part resin.

In the present invention, eluent collected from the container can be subjected to conventional methods such as concentration and desiccation to obtain extract of conjugated estrogens mixture. The extract can be further purified to produce qualified formulations used for drug preparation.

By using the pharmaceutically acceptable styrene-divinylbenzene semipolar macroporous adsorption resin with ester group structure to obtain conjugated estrogens mixture from PMU, the present invention overcomes the deficiencies existed in conventional methods of liquid-liquid extraction, thus solves the problems of low adsorption capacity, high cost, and ineffectiveness when dealing with PMU with different contents by conventional resins. The method of the present invention is efficient, cost-effective, environment friendly, and suitable for large-scale manufacture.

MODE FOR CARRYING OUT THE INVENTION

The present invention provides a method of obtaining a conjugated estrogens mixture from PMU by using macroporous adsorption resin, comprising the steps of a. pretreating raw pregnant mare urine; b. adsorbing from the pregnant mare urine a conjugated estrogens mixture with a macroporous adsorption resin; c. washing the macroporous adsorption resin adsorbed with the conjugated estrogens mixture by an alkaline aqueous solution; and (d). eluting the macroporous adsorption resin to obtain the conjugated estrogens mixture, wherein the macroporous adsorption resin is selected from styrene-divinylbenzene semipolar macroporous adsorption resins with ester group structure.

According to the method of the present invention, PMU should be pretreated before use to produce clear urine containing less mechanical impurities. The purpose of the pretreatment is to prevent the possible influence of the impurities in PMU on property of the resin during adsorption process. Pretreatment includes precipitation and/or filtration. Generally, the upper part of PMU will become relatively clear after 24 hours' natural standing. Alternatively, mechanical methods such as centrifugation can also be used to make PMU clear. Where there is a need for clearer PMU, routine filtration process can be carried out with plate filters, membrane filters, ultra-filters, etc. To obtain clearer PMU, the combination of filtration and centrifugation can also be used. For instance, PMU can be firstly subjected to natural precipitation and/or mechanical precipitation, and then go through filtration.

According to the method of the present invention, the semipolar macroporous adsorption resins are certain new types of macroporous adsorption resins. Different from other resins used in conventional methods for extracting conjugated estrogens mixture from PMU, the new types of resins are styrene-divinylbenzene semipolar macroporous adsorption resins having ester group(s), with middle polarity and cross-linked structure. The examples of such resins include HPD-400, HPD-400A, HPD-450, and HPD-100 resins from CangZhou Baoen company, and AB-8 resin from the Chemical Plant of Tianjin University.

In the dynamic adsorption method of the present invention, one part of the styrene-divinylbenzene semipolar macroporous adsorption resin with ester group structure can adsorb up to 150 parts of PMU, and preferably, 40-100 parts of PMU.

According to the method of the present invention, alkaline aqueous solution can be used to wash the macroporous adsorption resin adsorbed with the conjugated estrogens mixture, to remove impurities other than the conjugated estrogens mixture. The pH of the alkaline aqueous solution should be in the range of 11 to 14. The temperature of the solution is in the range of 20 to 80°. The washing volume of the alkaline aqueous solution is 2 to 10 times that of the resin.

According to the method of the invention, polar organic solvents or the mixture of a basic polar organic solvent and water can be used as an eluent to remove conjugated estrogens mixture from the macroporous adsorption resin. The eluent can be at least one organic solvent of lower alcohols and/or lower ketones, which are miscible with water. Alternatively, the eluent is a mixture of water and at least one organic solvent of lower alcohols and/or lower ketones, the pH of which is adjusted to 9.0-14.0 by basic substances. Lower alcohol, as used herein, refers to alkyl alcohols with 1-4 carbons, such as methanol, ethanol, iso-propanol, or butanol, which are miscible with water. Lower ketone, as used herein, refers to aliphatic ketones with 3-5 carbons, such as acetone, which are miscible with water.

The present invention will be illustrated by way of examples. It should be understood, however, the invention is not intended to be limited to the examples. It would be obvious to those skilled in the art that various other changes and modifications can be made without departing from the spirit and scope of the invention.

In the following examples, 100 ml of HPD-400 resin of the present invention was loaded to a column with 2.4 cm(diameter)×30 cm(height).

EXAMPLES

Example 1

After 24 hours' precipitation and ultrafiltration, 7,000 ml of clear PMU (the content of the conjugated estrogens mixture is 115.1 mg/L) was loaded to the adsorption column at ambient temperature at a flow speed of 500 ml/h. The adsorption ratio is 1:70. In the end of the adsorption process, the outflow was collected for HPLC assay. The result of the assay indicated only 4.01 mg/L of the conjugated estrogens mixture retains in the outflow. The loaded resin was then washed by 600 ml of sodium hydroxide aqueous solution (pH=12.0, temperature=30° C.) at a flow speed of 300 mL/h, followed by being eluted with 500 ml of eluent (methanol: acetone: water=20:30:50; pH was adjusted to 13 by sodium hydroxide; eluting temperature=20° C.) at a flow speed of 500 mL/h. 500 ml eluent was collected and subjected to HPLC assay to determine the concentration of the conjugated estrogens mixture in the eluent.

Example 2

After filtrated by a plate filter, 15,000 ml of clear PMU (the content of the conjugated estrogens mixture is 56.7 mg/L) was loaded to the adsorption column at ambient temperature at a flow speed of 600 ml/h. The adsorption ratio is 1:150. In the end of the adsorption process, the outflow was collected for HPLC assay. The result of the assay indicated only 9.55 mg/L of the conjugated estrogens mixture retains in the outflow. The loaded resin was then washed by 500 ml of potassium hydroxide aqueous solution (pH=13.0, temperature=40° C.) at a flow speed of 500 mL/h, followed by being eluted with 700 ml of eluent (methanol: water=20:80; pH was adjusted to 11 by sodium carbonate; eluting temperature=40° C.) at a flow speed of 700 mL/h. 700 ml eluent was collected and subjected to HPLC assay to determine the concentration of the conjugated estrogen in the eluent.

Example 3

After 12 hours' precipitation and membrane filtration, 4,000 ml of clear PMU (the content of the conjugated estrogens mixture is 216.4 mg/L) was loaded to the adsorption column at ambient temperature at a flow speed of 300 ml/h. The adsorption ratio is 1:40. In the end of the adsorption process, the outflow was collected for HPLC assay. The result of the assay indicated only 5.72 mg/L of the conjugated estrogens mixture retains in the outflow. The loaded resin was then washed by 400 ml of sodium hydroxide aqueous solution (pH=14.0, temperature=60° C.) at a flow speed of 400 mL/h, followed by being eluted with 650 ml of eluent (ethanol: water=55:45; pH was adjusted to 14 by potassium hydroxide; eluting temperature=60° C.) at a flow speed of 650 mL/h. 650 ml eluent was collected and subjected to HPLC assay to determine the concentration of the conjugated estrogen in the eluent.

Example 4

After 24 hours' precipitation, 6,000 ml of clear PMU (the content of the conjugated estrogens mixture is 140.2 mg/L) was loaded to the adsorption column at ambient temperature at a flow speed of 400 ml/h. The adsorption ratio is 1:60. In the end of the adsorption process, the outflow was collected for HPLC assay. The result of the assay indicated only 7.93 mg/L of the conjugated estrogens mixture retains in the outflow. The loaded resin was then washed by 800 ml of sodium carbonate aqueous solution (pH=11.0, temperature=20° C.) at a flow speed of 800 mL/h, followed by being eluted with 400 ml of eluent (n-butanol: water=90:10; pH was adjusted to 12 by sodium hydroxide; eluting temperature=30° C.) at a flow speed of 300 mL/h. 400 ml eluent was collected and subjected to HPLC assay to determine the concentration of the conjugated estrogen in the eluent.

The results of the examples were summarized in Table 1, which indicate the resins of the present invention have excellent adsorption ability to various contents of conjugated estrogens mixture in PMU. The highest adsorption ratio of the resin reaches 150 parts PMU/1 part resin, much superior to those disclosed in conventional arts. The step of washing with alkaline solution and the eluting step of the method according to the present invention can easily remove the conjugated estrogens mixture from the resin with high yield. The resin used in the present invention has high adsorption capacity and is easy to elute, totally complying with the requirement for resins used in extracting process.

The examples described above achieved relatively good result. According to practical needs, the styrene-divinylbenzene semipolar macroporous adsorption resins with ester group structure used in the invention can also be used in conventional PMU extracting processes with routine technical means and control parameters to solve the problems the invention intends to solve and achieve the technical effect of the invention.

In sum, the present invention overcomes the deficiencies existed in conventional methods of liquid-liquid extraction, thus solves the problems of low adsorption capacity, high cost, and ineffectiveness when dealing with PMU with different contents by conventional resins. The method of the present invention is efficient, cost-effective, environment friendly, and very suitable for large-scale manufacture.

| Procedures | Items | Unit | Example 1 | Example 2 | Example 3 | Example 4 |
|---|---|---|---|---|---|---|
| Pretreatment | Precipitation and/or filtration | | Precipitation for 24 hours + ultrafiltration | Plate filtration | Precipitation for 12 hours+ membrane filtration | Precipitation for 24 hours |
| Adsorption | Amount of PMU | mL | 7000 | 15000 | 4000 | 6000 |
| | Content of conjugated estrogens mixture | mg/L | 115.1 | 56.7 | 216.4 | 140.2 |
| | Adsorption speed of PMU | mL/h | 500 | 600 | 300 | 400 |
| | Volume adsorption ratio of PUM:resin | | 70:1 | 150:1 | 40:1 | 60:1 |
| | Contents of conjugated estrogens mixture in the outflow in the end of adsorption process | mg/L | 4.01 | 9.55 | 5.72 | 7.93 |
| Washing | Substances used to adjust the pH of the alkaline washing solution | | sodium hydroxide | potassium hydroxide | sodium hydroxide | sodium carbonate |
| | Volume of the alkaline washing solution | mL | 600 | 500 | 400 | 800 |
| | pH of the alkaline washing solution | | 12 | 13 | 14 | 11 |
| | Temperature of the alkaline washing solution | ° C. | 30 | 40 | 60 | 20 |
| Eluting | Volume of the eluent | mL | 500 | 700 | 650 | 400 |
| | Temperature of the eluent | ° C. | 20 | 40 | 60 | 30 |
| | Substances used to adjust the pH of the eluent | | sodium hydroxide | sodium carbonate | potassium hydroxide | sodium hydroxide |
| | Composition of the eluent | | Methanol:acetone:water | Methanol:water | ethanol:water | n-butanol:water |
| | Ratio of organic solvent(s):water in the eluent | | 20:30:50 | 20:80 | 55:45 | 90:10 |
| | pH of the eluent | | 13 | 11 | 14 | 12 |
| | Volume of the eluent collected | mL | 500 | 700 | 650 | 400 |
| | Concentration of conjugated estrogens mixture in eluent collected | mg/L | 1552.1 | 1111.7 | 1293.1 | 1995.7 |
| | Total extraction yield | | 96.3% | 91.5% | 97.1% | 94.9% |

What is claimed is:

1. A method of obtaining conjugated estrogen mixture from pregnant mare urine (PMU), comprising the steps of a. pretreating raw PMU;

b. adsorbing conjugated estrogens mixture in PMU with a macroporous adsorption resin;

c. washing the macroporous adsorption resin adsorbed with the conjugated estrogens mixture by an alkaline aqueous solution;

d. eluting the macroporous adsorption resin with an eluent to obtain conjugated estrogens mixture;

wherein the macroporous adsorption resin is a styrene-divinylbenzene semipolar macroporous adsorption resin with ester group structure.

2. The method of claim 1, wherein the styrene-divinylbenzene semipolar macroporous adsorption resin with ester group structure is formed by the polymerization of carboxylate and styrene-divinylbenzene.

3. The method of claim 2, wherein the average diameter of the styrene-divinylbenzene semipolar macroporous adsorption resins with ester group structure is in the range of 50-120 Å, and the specific surface of the resin is in the range of 400-1000 $m^2/g$.

4. The method of claim 3, wherein the styrene-divinylbenzene semipolar macroporous adsorption resins with ester group structure is at least one semipolar macroporous adsorption resin type selected from the group consisting of HPD-400, HPD-400A, HPD-450, HPD-100, and AB-8.

5. The method of claim 1, wherein in step c, at a temperature of 20° C. to 60° C., an alkaline aqueous solution with a pH of 11.0-14.0 is used to wash the macroporous adsorption resin adsorbed with the conjugated estrogens mixture, and/or in step d, at a temperature of 20° C. to 60° C., an aqueous solution of polar organic solvent of lower alcohols and/or lower ketones, which is miscible with water, is used as an eluent to elute the macroporous adsorption resin to obtain the conjugated estrogens mixture, the pH of the eluent being 9 to 14, and the volume ratio of the polar organic solvent to water being 90:10 to 20:80.

6. The method of claim 5, wherein the alkaline aqueous solution is an inorganic basic aqueous solution, sodium hydroxide aqueous solution, potassium hydroxide aqueous solution, sodium carbonate aqueous solution, potassium carbonate aqueous solution, potassium bicarbonate aqueous solution, or sodium bicarbonate aqueous solution, the washing volume of the alkaline aqueous solution is 2 to 10 times that of the adsorption resin, and the speed of the alkaline aqueous solution flowing through the container filled with the adsorption resin is 3-10 times volume of adsorption resin in 1 hour.

7. The method of claim 5, wherein the lower alcohol used in the eluent is methanol, ethanol, n-propanol, iso-propanol, or butanol, the lower kenone used in the eluent is acetone or butanone, the amount of the eluent is 2 parts - 10 parts/ 1 part adsorption resin, and the speed of the alkaline aqueous solution flowing through the container filled with the adsorption resin is 3-10 times volume of adsorption resin in 1 hour.

* * * * *